United States Patent [19]

Rice

[11] Patent Number: 5,008,449
[45] Date of Patent: Apr. 16, 1991

[54] METHOD OF SYNTHESIS OF HYDROXY-SUBSTITUTED-4-ALKOXY-PHENYLACETIC ACIDS

[75] Inventor: Kenner C. Rice, Bethesda, Md.

[73] Assignee: The United States of America as represented by the Department of Health and Human Services, Washington, D.C.

[21] Appl. No.: 318,590

[22] Filed: Mar. 3, 1989

[51] Int. Cl.$^5$ ............................................. C07C 65/01
[52] U.S. Cl. ..................................................... 562/478
[58] Field of Search ........................................ 562/478

[56] References Cited

U.S. PATENT DOCUMENTS 1,529,946  3/1925  Dubin et al. .
2,228,920  1/1941  Eckert et al. .
2,240,275  4/1941  Whitmore et al. .
3,086,990  4/1963  Reeve .
4,390,723  6/1983  Matsuno ............................. 562/478

OTHER PUBLICATIONS

Weller et al., *J. Org. Chem.*, 49:2061–2063, (1984).

*Primary Examiner*—Paul J. Killos
*Attorney, Agent, or Firm*—Robert Benson

[57] ABSTRACT

A process for preparing hydroxy-substituted-4-alkoxyphenylacetic acids by reacting a 4-alkoxyphenylacetic acid with bromine and then treating the brominated acid with a strong base and a copper salt to form the desired hydroxy-substituted-4-alkoxyphenylacetic acid.

5 Claims, No Drawings

METHOD OF SYNTHESIS OF HYDROXY-SUBSTITUTED-4-ALKOXYPHENYLACETIC ACIDS

FIELD OF THE INVENTION

The present invention relates to the improved synthesis of hydroxy-substitued-4-alkoxyphenylacetic acids.

BACKGROUND OF THE INVENTION

Oxygen-substituted phenylacetic acids are known compounds which have been used in the synthesis of a wide variety of natural products, including flavonoids and alkaloids. Of these, 3-hydroxy-4-methoxyphenyl acetic acid is one of the basic raw materials for the synthesis of natural and unnatural opium derivatives, including antagonists and agonist-antagonists. More particularly, the present inventor has used 3-hydroxy-4-methoxyphenylacetic acid in a concise synthesis of the opiate precursor dihydrothebainone, *J. Oro. Chem.* 45: 3135, 1980. Prior methods have one or more of the disadvantages of requiring high pressure, high reaction temperature, undue use of hazardous solvents such as ether and producing product in low yield and impure state.

Weller et al, in *J. Org. Chem.* 49:2061–2063 (1984) disclose a method for synthesizing oxygenated phenylacetic acids by brominating 4-methoxyphenylacetic acid and then displacing the bromine by hydroxide in a copper-catalyzed reaction under pressure.

Reeve, in U.S. Pat. No. 3,086,990, discloses a process for producing m-chloro- and m- and p-fluoroalpha-methoxyphenylacetic acid from the corresponding halogenated benzaldehydes in bromoform with potassium hydroxide in methanol.

Eckert et al, in U.S. Pat. No. 2,228,920, disclose a process for preparing 5-hydroxy-trimellitic acid by treating a 5-halogen pseudocumene with an oxidizing agent and heating the obtained 5-halogentrimellitic acid with an alkali or an agent having an alkaline reaction.

Dubin et al, in U.S. Pat. No. 1,529,946, disclose a process for preparing fatty acids of the acetic acid series from their higher homologs by converting the acid to the corresponding halogen acid, treating the halogen acid with an alkaline reagent capable of replacing the halogen by a hydroxyl group, oxidizing the hydrolyzed product of the alkaline treatment, and recovering the resulting acid. Each procedure produces an acid containing one less carbon atom than the acid so treated.

Whitmore et al, in U.S. Pat. No. 2,240,275, disclose a method for preparing highly branched brominated organic acids by treating the starting acid with liquid bromine in the presence of a catalyst so that the bromine becomes attached to the carbon atom in the alpha position with respect to the carboxy radical.

SUMMARY OF THE INVENTION

It is an object of the present invention to overcome the deficiencies in the prior art, such as noted above.

It is another object of the present invention to provide an improved synthesis method for hydroxysubstituted-4-alkoxyphenylacetic acids.

It is a further object of the invention to provide a method for synthesizing hydroxy-substituted-4-alkoxyphenylacetic acid wherein no stage of the reaction must be conducted under high pressure.

It is another object of the present invention to use a significantly lower reaction temperature for the synthesis than does the prior art.

It is yet a further object of the present invention to provide a method of synthesis for hydroxysubstituted-4-alkoxyphenyl acetic acids which does not require isolation of any of the product by extraction with a hazardous organic solvent such as ether.

It is still another object of the present invention to provide a method for synthesizing hydroxysubstituted-4-alkoxy-phenylacetic acids which requires lower molar ratios of reactants to provide a substantially pure product in high yield.

According to the present invention, a 4-alkoxy-substituted-phenylacetic acid starting material is brominated in a suitable solvent, such as chloroform at reflux. The solvent is removed, and water is added along with a base to neutralize the acid. A copper salt is added, and the reaction mixture is heated at 100°–120° C. to form the desired hydroxy-substituted-4-alkoxyphenylacetic acid. The copper salts may be selected form any water-soluble copper salts, such as copper sulfate, copper chloride, and the like. The strong base may be sodium hydroxide, potassium hydroxide, or the like, such as lithium hydroxide, barium hydroxide, or calcium hydroxide.

The reaction scheme is as follows:

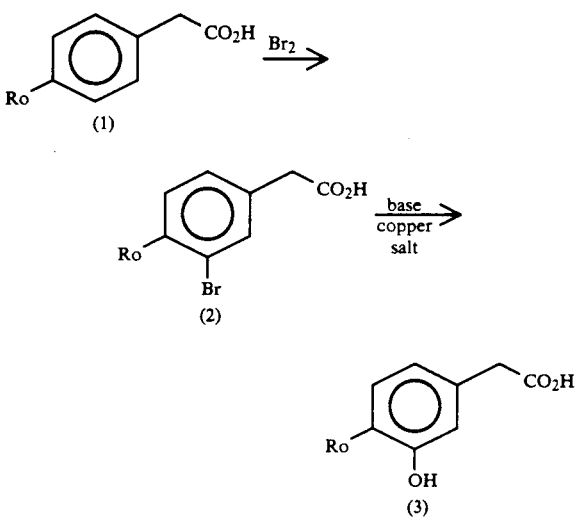

Wherein R is $C_1$–$C_3$ alkyl.

The present invention overcomes the disadvantages of the prior art by not isolating the first intermediate (2) in the process, and by utilizing a much more concentrated reaction mixture in the second step. This eliminates the requirements for a pressure reactor. The process of the present invention also uses a significantly lower temperature than the prior art, and avoids isolation of the product by extraction with a hazardous organic solvent such as ether.

For isolation of the product, the process of the present invention requires only acidification, filtering, and washing with water to isolate the product in approximately 89% yield of material which is more than 97% pure and suitable for direct use in the total synthesis of opiates.

In summary, the advantages of the present invention over that of the prior art are:

(a) The use of atmospheric pressure reaction conditions rather than high pressure reaction conditions;

(b) The ability to use much higher concentration of reactants, e.g. 40% rather than 1% thus obviating the necessity of using large amounts of solvents;

(c) Ease of isolation of the product by filtration rather than ether extraction;

(d) Lower reaction temperatures of from about 109°–115° C. rather than 150° C.; and (e) Lower molar ratios of base and copper salts to the bromo intermediate by factors of 7.4 and 3, respectively.

In the process of the present invention, the base is used in a molar ratio of about 8 to 1 relative to the bromo intermediate, and the copper salt is used in a molar ratio of about 0.065 to 1.

The advantages of the process of the present invention over the prior art render the process of the present invention a nearly ideal manufacturing process for preparation of hydroxy-substituted-4-alkoxyphenylacetic acids.

DETAILED DESCRIPTION OF THE INVENTION

The following example describes the preparation of 3-hydroxy-4-methoxyphenylacetic acid. Depending upon the hydroxy substitution desired, the starting material can be changed to reflect this desired hydroxy substitution. Additionally, the alkoxy substitution can be methoxy, ethoxy, propoxy, isopropoxy, butoxy, or t-butoxy.

The reaction of 3-hydroxyphenylacetic acid to 3-hydroxy-4-methoxyphenylacetic acid is as follows:

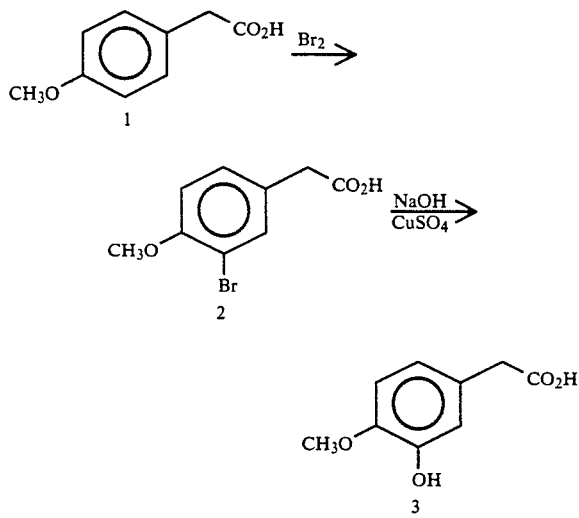

A mechanically stirred mixture of 4-methoxyphenylacetic acid, compound 1 (166.2 grams, 1.0 mol) and 300 ml chloroform, was heated to reflux and treated during a period of 4.5 hours with a solution of 55 ml bromine (1.07 mol) in 175 ml chloroform. The mixture was refluxed for fifteen hours, after which time no starting material and only traces of bromine remained. The chloroform was distilled under aspirator vacuum until the batch temperature reached 90° C.

Two hundred ml of water was added, and the mixture was distilled at atmospheric pressure to remove the last of the chloroform, until 50 ml of water was collected. Fifty ml of water was then added, and 60 grams (1.5 mol) of sodium hydroxide was added to the stirred mixture in small portions, maintaining a batch temperature of 80°–90° C. with ice bath cooling. The mixture was distilled to collect 70 ml of ethanol and water.

The mixture was then diluted with 70 ml water and transferred to a one liter polypropylene bottle with 200 ml of water, treated with 260 grams (6.5 mol) of sodium hydroxide, and stirred under argon for ten minutes with a 316 stainless steel shaft to give a smooth slurry of the sodium salt of compound 2.

A solution of $CuSO_4.5H_2O$ (16.4 grams, 0.0656 mol) in 200 ml water was added in a thin stream. The dark slurry was stirred under argon and heated at 109°–115° C. internal temperature for forty hours. During the first three hours of heating, the mixture gradually became yellow and homogeneous. A glycerine bath accurately controlled at 125°–130° C. with a Therm-0-Watch was used for heating.

At the end of the heating period an aliquot was treated as follows for analysis: Two drops of the reaction mixture was acidified with 37% HCl, and extracted with 4×1 ml ether. The extract was evaporated to dryness, dissolved in 0.5 ml methanol, and saturated with HCl gas. The mixture was boiled for one minute and evaporated under a stream of nitrogen.

Gas chromatographic analysis on an OV-1 capillary column (140° C. for six minutes, then 30° C./m to 250° C. for six minutes) showed 0.6% of compound 2 remaining, 1.7% of compound 1 from reduction of the intermediate 2, and 94.6% of product 3. The mixture was cooled, partially neutralized with 332 ml of 37% HCl, filtered through celite using 250 ml of water for transfer and wash of the filter. The stirred filtrate was acidified at 10°–15° C. by the dropwise addition of 268 ml of 37% HCl. The crystalline product, compound 3, was filtered, pressed, and washed well with 3×125 ml of water at 5° C. The last filtrate gave a negative test for chloride ion with 10% aqueous silver nitrate. Drying in a vacuum oven at 70° C. overnight gave 162.07 grams, or 89%, of product 3 as light tan crystals: mp (corrected) 125°–129° C. (clear melt). Conversion to the methyl ester as above and gas chromatographic analysis showed 1.6% of compound 1, 0.4% of compound 2, and 97.4% of product 3. For laboratory preparation of product 3, a polypropylene reaction vessel was used in the hydrolysis step to avoid introducing significant amounts of silicate to the reaction mixture by reaction of glass with the strong base. In an industrial manufacturing environment, a stainless steel reactor can conveniently be used.

The 3-hydroxy-4-methoxyphenylacetic acid so produced has been found to be satisfactory for opiate total synthesis as directly obtained as shown by its conversion to the racemic 1,2,3,4-tetrahydroisoqunioline intermediate, compound 4, for the opiate total synthesis as described in U.S. Pat. Nos. 4,368,326; 4,410,700; 4,556,712; 4,521,601; and 4,613,668 to Rice. The yield in this step was 90.6% of unpurified material which showed a melting point of 193°–197.5° C. and was satisfactory for use in the next step.

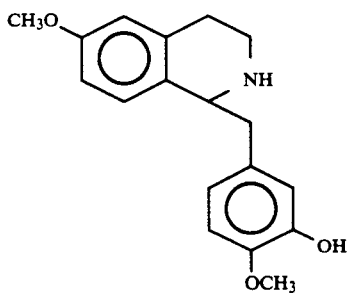

3-hydroxy-4-methoxyphenylacetic acid, compound 3, can be purified should this be required for other applications. The approximately 80% ethanol used as described below was prepared by dilution of 85 ml of commercial 95% ethanol to 100 ml with deionized water. A sample of compound 3 (74.5 grams, 0.409 mol) from a previous, unoptimized run which was much darker than that prepared as described above was used and showed 1.9% compound 1, 0.03% compound 2, and 98.1% compound 3, corrected melting point 123°–127° C. This material was dissolved in 80 ml of 80% ethanol and added to a solution of 87.5% potassium hydroxide (25.9 grams, 0.404 mol) in 122 ml of 85% ethanol using 25 ml of 85% ethanol for the transfer. The mixture was cooled to 5° C. and the potassium salt of compound 3 was filtered and washed with 80 ml of 80% ethanol and air dried to give 91.98 grams of the salt. The filtrate and washings were evaporated to a semisolid which was heated to solution in 30 ml of 80% ethanol and cooled to 5° C.

The resulting crystals were filtered, washed with 15 ml of 80% ethanol and air dried to give 5.06 grams of the salt. The first and second crops were combined and heated to solution in 145 ml water at 80° C. and treated with 40 ml of 37% HCl in one portion. The mixture was cooled to 5° C. to give a thick slurry of acid, compound 3, which was filtered, pressed well, and washed with 4×50 ml water. The filtrate from the last wash gave a negative test for chloride ion with 10% aqueous silver nitrate. Air drying to constant weight gave 66.11 grams (88.8% recovery) of the acid compound 3, corrected melting point 130°–132° C. Analysis as described above showed 0.2% of compound 1 and 99.8% of compound 3 as the only components.

While the invention is described above in relation to certain specific embodiments, it will be understood that many variations are possible, and that alternative materials and reagents can be used without departing from the invention. In some cases such variations and substitutions may require some experimentation, but such will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A method of synthesizing 3-hydroxy-4-alkoxyphenylacetic acid comprising the following steps:
   (I) reacting 4-alkoxyphenylacetic acid with bromine to produce 3-bromo-4-alkoxyphenylacetic acid; and
   (II) reacting said 3-bromo-4-alkoxyphenylacetic acid with water, strong base and a water-soluble copper salt at a temperature of 100°–120° C., and wherein the reaction mixture of step II is sufficiently concentrated such that the reaction is run at atmospheric pressure.

2. The method of claim 1, wherein the alkoxy group of said 4-alkoxyphenylacetic acid is chosen from the group consisting of methoxy, ethoxy, propoxy, isopropoxy, butoxy and t-butoxy.

3. The method of claim 2, wherein the reaction of step II is run at a temperature of 109°–115° C.

4. The method of claim 3, wherein the molar ratio of said strong base to said 3-bromo-4-alkoxyphenylacetic acid is about 8 to 1, and the molar ratio of said soluble copper salt to said 3-bromo-4-alkoxyphenylacetic acid is about 0.065 to 1.

5. The method of claim 4, wherein said strong base is chosen from the group consisting of sodium hydroxide, potassium hydroxide, lithium hydroxide, barium hydroxide and calcium hydroxide, and said soluble copper salt is chosen from the group consisting of copper sulfate and copper chloride.

* * * * *